(12) United States Patent
Clark

(10) Patent No.: US 6,828,908 B2
(45) Date of Patent: Dec. 7, 2004

(54) LOCATOR SYSTEM WITH AN IMPLANTED TRANSPONDER HAVING AN ORGANICALLY-RECHARGEABLE BATTERY

(76) Inventor: Ronald Scott Clark, P.O. Box 878, Bruce, MS (US) 38915

( * ) Notice: Subject to any disclaimer, the term of this patent is extended or adjusted under 35 U.S.C. 154(b) by 113 days.

(21) Appl. No.: 10/072,442

(22) Filed: Feb. 6, 2002

(65) Prior Publication Data

US 2003/0151524 A1 Aug. 14, 2003

(51) Int. Cl.[7] .................................................. G08B 1/08
(52) U.S. Cl. ............................. 340/539.13; 340/539.14; 340/545.4; 340/573.1; 340/10.1
(58) Field of Search ....................... 340/539.13, 539.14, 340/539.15, 539.16, 539.17, 539.1, 539.11, 545.4, 573.1, 573.3, 10.1, 10.3, 10.34, 10.4, 10.42, 10.52

(56) References Cited

U.S. PATENT DOCUMENTS

| | | | |
|---|---|---|---|
| 3,588,858 A | | 6/1971 | Demuth |
| 4,854,328 A | | 8/1989 | Pollack |
| 5,721,783 A | * | 2/1998 | Anderson .................... 381/328 |
| 5,731,785 A | * | 3/1998 | Lemelson et al. ..... 342/357.07 |
| 5,742,233 A | * | 4/1998 | Hoffman et al. ......... 340/573.1 |
| 5,752,976 A | * | 5/1998 | Duffin et al. ................. 607/32 |
| 5,767,791 A | * | 6/1998 | Stoop et al. ........... 340/870.11 |
| 5,838,237 A | | 11/1998 | Revell et al. |
| 5,952,959 A | | 9/1999 | Norris |
| 6,034,622 A | | 3/2000 | Levine |
| 6,169,494 B1 | | 1/2001 | Lopes |
| 6,239,705 B1 | | 5/2001 | Glen |
| 6,243,039 B1 | | 6/2001 | Elliot |
| 6,263,280 B1 | | 7/2001 | Stingone, Jr. |
| 6,268,798 B1 | | 7/2001 | Dymek et al. |
| 6,278,370 B1 | | 8/2001 | Underwood |
| 6,285,289 B1 | | 9/2001 | Thornblad |
| 6,317,049 B1 | * | 11/2001 | Toubia et al. ............. 340/573.4 |
| 6,559,620 B2 | * | 5/2003 | Zhou et al. ................. 320/101 |

* cited by examiner

Primary Examiner—Jeffery Hofsass
Assistant Examiner—Daniel Prévil
(74) Attorney, Agent, or Firm—Michael I. Kroll

(57) ABSTRACT

A locator device having a transponder subcutaneously implanted in a person or animal that is to be periodically monitored in the event of emergency, abduction and other such situations. The transponder has a battery that is rechargeable by using the potential electrical energy generated by the body of the host organism. The preferred embodiment of the rechargeable transponder uses a piezo-electric battery that is to be implanted in an appropriate manner that would permit a large muscle to act upon a piezoelectric element thereby converting the mechanical energy into electrical energy to provide a recharge to the battery.

9 Claims, 8 Drawing Sheets

LOCATOR SYSTEM WITH AN IMPLANTED TRANSPONDER HAVING AN ORGANICALLY-RECHARGEABLE BATTERY

BACKGROUND OF THE INVENTION

FIELD OF THE INVENTION

The present invention relates generally to locator devices and, more specifically, to a locator device having a biocompatible transponder that is subcutaneously implanted in a human or animal to selectively transmit positional data to a remote locator device in the event that the subject is lost, missing or in need of being monitored. Furthermore, the transponder has a renewable power source that utilizes the host organism to supply a recharge thereto thereby negating the need for the periodic removal thereof. The renewable power source is preferably a piezoelectric battery that utilizes the piezo effect—a material's capacity to convert mechanical energy to electrical energy—to maintain a fully charged battery until needed and to effectively recharge it thereafter. Each transponder is set to it's own specific frequency and is activated when the user seeking the subject inserts the subjects PIN into the locator unit thereby sending out the appropriate signal to activate the implanted transponder which then returns the signal thus enabling the locator unit to define the precise location of the subject. A voice activation feature similar to voice dialing in cellular telephones could be included in the transponder and would allow the user to unilaterally activate the transponder by stating a predetermined password.

An alternate renewable power source that harnesses and stores energy available from the host organism is a bioelectric transponder battery that uses the considerable amount of electricity in the human body involving regulatory, metabolic and healing processes such as that generated by the nervous system and transferred by neurotransmitters. The bioelectric battery has contacts that act as neurotransmitter receptors to scavenge electricity from areas with high concentrations of action potential where synaptic and/or neuromuscular transmission occur which could also include the heart and spinal cord.

Certain applications of the present invention may require more frequent usage than other applications thereby using more electricity than could be restored by the microamperage of the trickle charge supplied to the bioelectric battery by the host organism's nervous system. For instance, a government agent or soldier in the field may require frequent monitoring as opposed to a child or fireman that would only have the transponder activated in emergency situations, therefore an external charger is also available to rapid charge the bioelectric battery by passing an electrical current through the body in a similar manner to that of the bioelectric therapy that is frequently used in holistic and conventional medicine. One embodiment of the bioelectric battery charger plugs into a standard DC outlet and has a step down transformer that produces a high frequency low voltage electric current and has two leads extending therefrom that are placed in contact with the epidermal tissue of opposing limbs of the implanted subject so the current could pass therethrough. High frequency current is used because it penetrates all body tissues whereas low frequency current flows primarily through extracellular fluids.

Thermal batteries that recharge by using the heat generated by a human body are currently in development for pacemakers and other like applications and could provide another viable option of harnessing the potential energy of the human body.

The present invention has many applications in military and civilian life that vary from allowing government agencies to monitor and track EMS workers, troops, commandos, intelligence agents and other such field operatives to parents who want to monitor their children or insure a quick recovery in case of kidnapping or abduction. The present invention provides an undetectable GPS location means that cannot be removed from the monitored subject like similar locator devices that are integral with clothes and jewelry and the like. Moreover, the piezoelectric battery that powers the transponder converts the kinetic energy created by the muscular contraction and extension of the host organism to electrical energy that is stored therein to provide a continuous charge thereto thus avoiding the necessity of having to invasively remove the implant to access the battery for recharging or replacement purposes.

An alternate embodiment of the present invention is a GPS locator device having a transponder that may be worn as jewelry or integrated within the clothing of the subject to be monitored. This noninvasive locator system could be part of the uniforms used by police or firemen so they could be readily located when on duty. A child could wear the transponder as a bracelet, necklace or other like ornamental device. Furthermore, a speaker/microphone could be provided to allow for voice activation and instantaneous two-way communication with a central office.

DESCRIPTION OF THE PRIOR ART

There are other GPS locator devices. Typical of these is U.S. Pat. No. 3,588,858 issued to Demuth on Jun. 28, 1971.

Another patent was issued to Pollack on Aug. 8, 1989 as U.S. Pat. No. 4,854,328. Yet another U.S. Pat. No. 5,731,785 was issued to Lemelson et al. on Mar. 24, 1998 and still yet another was issued on Nov. 17, 1998 to Revell et al. as U.S. Pat. No. 5,838,237.

Another patent was issued to Norris on Sep. 14, 1999 as U.S. Pat. No. 5,952,959. Yet another U.S. Pat. No. 6,034,622 was issued to Levine on Mar. 7, 2000. Another was issued to Lopes on Jan. 2, 2001 as U.S. Pat. No. 6,169,494 and still yet another was issued on May 29, 2001 to Glen as U.S. Pat. No. 6,239,705.

Another patent was issued to Elliot on Jun. 5, 2001 as U.S. Pat. No. 6,243,039. Yet another U.S. Pat. No. 6,263,280 was issued to Stingone Jr. on Jul. 17, 2001. Another was issued to Dymek et al. on Jul. 31, 2001 as U.S. Pat. No. 6,268,798 and still yet another was issued on Aug. 21, 2001 to Underwood as 6,278,370. A patent was issued to Thornblad as U.S. Pat. No. 6,285,289 on Sep. 4, 2001. On Jul. 16, 1998 a patent was issued to Grunchi et al. as German Patent No. DE 197 00 614 A1 and on Sep. 23, 1987 O'Brien was issued UK Patent No. GB 2 188028 A. French Patent No. FR 2 692 777 was issued on Dec. 31 1993 to Cussett et al.

A safety alarm system designed for use by individuals working alone consisting of a radio transmitter which is activated by a position sensitive switch and a radio receiver which activates an alarm means which indicates that the person has been injured or otherwise incapacitated. The switch is selected to activate at any position which a person would normally assume if he were injured or incapacitated, such as a prone position. The transmitter can also be equipped with a manual switch in combination with a position-sensitive switch so that it can also be used as an alarm system even when the individual is not incapacitated.

An animal monitoring telltale device including a receiver attached to the animal and a transmitting device inserted in the animal subcutaneously or in a cavity at a location indicative of the deep body temperature of the animal. The implanted transmitter will send a signal to the proximately located receiver indicative of a monitored condition in the animal. In addition, the signal is encoded with an identification signal providing ownership information and theft protection. The receiver is preferably secured to an ear tag which tag includes a light or other visual signal indicative of a predetermined value of the measured condition. The receiver may also be operatively connected to a re-transmitter for re-transmitting a higher power signal to a remote monitoring location.

A system and method are provided for communicating between a person, object, and/or vehicle carried transceiver and a monitor station to locate and track the movement of the same for security or anti-crime purposes. A portable computing and communication device carried by a person or located (hidden) in an object generates and transmits via radio signals a plurality of codes when remotely activated. One (or more) code(s), identifying or descriptive of the person, object or vehicle to be tracked, is (are) generated and transmitted to a monitor station to display character and/or video picture information describing and/or physically displaying a picture of a select person and/or vehicle and license plate information to permit police or security personnel to recognize the same. Such coded information may be immediately transmitted or retransmitted from the monitor station to a radio receiver carried by a policeman or in one or more police vehicles.

A self-contained personal alarm device capable of signaling its location to a remote site such as a security station. The personal alarm device includes a housing enclosing a controller, an antenna, a cellular transmitter and a cellular receiver. The controller is coupled to the transmitter and receiver, which are in turn coupled to the antenna. The controller and the receiver to receive position location signals such as Global Positioning System signals (GPS), establish a cellular connection with a remote site, and transmit device location data to the remote site on the cellular connection, wherein the device location data indicates the location of the device. The cellular connection is established via a cellular network that includes an array of cell base stations. The GPS signals are transmitted to the device over the cellular network by providing each cell base station with a Differential Global Positioning System (DGPS) receiver. Using the DGPS receivers, GPS signals are repeated over the cellular network.

A system of GPS devices which receive civilian GPS signals and provide an intuitive graphical interface for displaying the relative position of GPS devices in relation to each other, the relative position being accurate to several meters and defined as the distance to, direction of and height variance between GPS devices. A first GPS device with the person or object to be located transmits its GPS determined location to a second GPS device. This second GPS device includes a means for receiving the GPS determined position of the first GPS device, and also includes means for calculating the relative position of the first GPS device relative to the second GPS device based on a comparison of the received telemetry of the first GPS device and its own GPS determined position. The relative position of the first device is then graphically displayed on an interface of the second GPS device in a manner which eliminates the need for a map in order to travel to the location of the first GPS device. While providing an interface which displays a relative position of the first GPS device, this information remains accurate no matter how the orientation of the second GPS device changes with respect to a compass.

An open-loop internal monitoring system comprising (a) a plurality of internal radio transmitters, each being implanted in a human for transmitting a plurality of signal pulses, each pulse being encoded with unique identifying information; (b) a plurality of external radio receivers each having a corresponding clock, for receiving each of the plurality of signal pulses transmitted by each of the plurality of internal radio transmitters and for generating from each received signal pulse a plurality of data including at least a time-of-arrival generated in accordance with the synchronized clock of the external radio receiver and the internal radio transmitter identifying information; and (c) a central processor for (1) estimating a location for each internal radio transmitter in accordance with the time-of-arrival, (2) storing, for each human, authorized or unauthorized areas to which the human is assigned, (3) determining an event of whether the estimated location is within the authorized area or the unauthorized area assigned to any one of the humans and stored in the central processor, and (4) notifying a monitor of the central processor upon occurrence of the event.

A biotelemetry tracking and locating system uses a person's own physical or biological measurement as an identification code used by a tracked unit, e.g., a bracelet worn by a child, to track and/or locate the person from a tracking/locating unit, e.g., worn or carried by a parent. The tracking/locating unit includes a transmitter and optionally a receiver. The tracking/locating unit detects a combination of encoded biological measurements (e.g. body temperature, and/or heart rate) and combines the biological measurements into a substantially unique ID code. The tracking/locating unit may be carried, e.g., by a parent to track the continued presence within a reception range of, e.g., a child wearing the tracked unit. A directional antenna, e.g., a YAGI type antenna, in the tracking/locating unit allows the tracking/locating unit to determine which direction the tracked unit is in, e.g., with respect to the tracking/locating unit. A panic button can be included with the tracked unit to allow a child or other person wearing a tracked unit to alert the tracking person, e.g., a parent to a dangerous situation. The tracking unit may include a paging button to output a paging signal to desired tracked units, which is emitted visually or aurally at the tracked unit.

An improved stealthy, non-surgical, biocompatable electronic tracking device is provided in which a housing is placed intraorally. The housing contains microcircuitry. The microcircuitry comprises a receiver, a passive mode to active mode activator, a signal decoder for determining positional fix, a transmitter, an antenna, and a power supply. Optionally, an amplifier may be utilized to boost signal strength. The power supply energizes the receiver. Upon receiving a coded activating signal, the positional fix signal decoder is energized, determining a positional fix. The transmitter subsequently transmits through the antenna a position locating signal to be received by a remote locator. In another embodiment of the present invention, the microcircuitry comprises a receiver, a passive mode to active mode activator, a transmitter, an antenna and a power supply. Optionally, an amplifier may be utilized to boost signal strength. The power supply energizes the receiver. Upon receiving a coded activating signal, the transmitter is energized. The transmitter subsequently transmits through the antenna a homing signal to be received by a remote locator.

A system that tracks the current and historical locations of a GPS locator device carried by a person provides widely available access to data referencing these locations, so that a parent can easily and frequently monitor the location of a child. Monitoring of a child's location may be conducted via a Web site, which provides graphical maps of location data, or via calling into a call center. The present invention also provides a means for a parent to trigger the automatic transmission of the device's location, via a Web site or call placed to a call center agent or a VRU. The present invention also provides a process of auto-notification of a device's movement that exceeds a pre-specified threshold. The present invention also includes a capability to function as a proximity alert device.

A method and system for locating and tracking the geographic position of a remote unit worn or carried by a user comprises a battery powered remote unit which upon user activation receives geographic position signals from geographic positioning satellites. The geographic position signals are encoded with a unique code associated with the remote unit and then transmitted from the remote unit to a central control center. The geographic position of the remote unit is determined according to the geographic position signals and then relayed to a computer network database server system. The geographic position along with personal information previously stored on the server system is then displayed at a network location such that a search for the wearer of the remote unit can be initiated by persons having access to the network location. Following initial activation, the remote unit receives and transmits signals only at predetermined time intervals so as to conserve battery power of the remote unit.

An emergency locator system (10) for firefighters (100) including a first housing unit (11) carried by a firefighter and containing a global positioning receiver unit (12), a memory unit (13), and a data transmitting unit (13) which communicates continuous positional data relative to the location of the first housing unit (11) to a central processing unit (15) that can store, retrieve, and transfer the positional data from the first housing unit (11) to a second housing unit (11') that includes at least a memory unit (60) that is associated with an LED array (40) having directional arrow icons (45) that are activated by the transferred positional data from the first housing unit (11) to permit rescuers to retrace the path of travel of the first housing unit (11) by using the second housing unit (11') to locate a disabled firefighter.

A child locating and tracking apparatus which provides for the location of a child that is lost, abducted or in general danger to be quickly located is disclosed. The apparatus uses a small transmitter that is always carried by the child and as such, is always present when danger arises. The transmitter is easily disguised and hidden in the child's clothing or personal adornments such as shoes, coats, watches, earrings, bracelets, rings and the like. The apparatus uses a system of world wide receivers such as those provided by local cellular telephone towers or by low earth orbiting satellites used for low power communication. When a child is lost or in danger, the child simply activates the transmitter which sends a signal to a central reporting station or stations where trained personnel will contact the respective parents and/or care givers to determine if the child could possibly be in danger. If an affirmative decision is reached, the monitoring station personnel will then assist the local law enforcement officials in the respective area anywhere in the world where the alarm was received in locating the child and removing the child from harm's path.

A self contained, wearable personal protection device that incorporates a silent security alarm feature, a smoke detector alarm feature and, optionally, the feature of providing the time of day to the wearer is disclosed. The personal protection device with these features is incorporated into a housing case that is sized to be worn about the wrist of an individual user. The personal protection device is particularly suited for use by children. The smoke detector alarm feature of the device automatically activates an audible alarm feature when smoke is detected. The silent security alarm feature is activated when the wearer pushes a button on the device. Further, the wrist worn personal protection device optionally provides the wearer with the time of day as a further incentive for the child to wear the device.

The system has at least one receiver for reception of a radio signal transmitted by a location transmitter (3). The receiver passes the signal to an evaluation unit which determines the position of the person in which the transmitter is implanted. The location transmitter implant (2) can be effected in a long bone (1), and has at least one surface at least partially provided with an open mesh, three-dimensional spatial network structure, and a liquid tight capsule which holds the location transmitter.

An electronic ear implant for identification of wild and domestic animals is inserted under the skin of ear with a syringe. It is held in place by between 10 and 500 spines to prevent removal. The implant comprises a metal, plastics, or silicone rubber tube housing a battery A, a radio-controlled switching timing device B, and a coded information electronic component connected to a short range transmitter C. When activated by an external radio frequency, the device is switched on and will transmit coded information indicating the herd number, individual animal number, year of birth and sex of the animal. The information held within the implant will be transmitted up to 3 metres, for a duration of between 5 and 20 seconds, after which time the device will switch off. The timing device will then remain in an off-mode until reactivated by the external radio frequency.

The implant control unit (1) includes a source of electrical energy (14), electronic circuits (11) and a transmitting antenna (10). The electronic circuits (11) include an oscillator and an amplifier to supply power to the transmitting antenna (10). The implant in the patients body has a receiving antenna with a tuning unit such as a variable capacitor adjusted to the transmitter oscillator. The energy received is rectified and fed to the implant. In operation it is only necessary to place the transmitting unit (1) close to the patient's implant and start the oscillator.

While these locator devices may be suitable for the purposes for which they were designed, they would not be as suitable for the purposes of the present invention, as hereinafter described.

SUMMARY OF THE PRESENT INVENTION

A primary object of the present invention is to provide a locator system having an undetectable irremovable transmitter means implanted subcutaneously in the person or animal to be monitored.

Another object of the present invention is to provide a locator system with an implanted biocompatible transponder having a battery that uses the host organism to provide a recharge thereto.

Still another object of the present invention is to provide a locator system with an implanted biocompatible transponder that transmits positional data to a remote locator unit either directly or by means of a relay system such as a global positioning satellite system, hereon referred to as GPS.

One other object of the present invention is to provide a locator system with an implanted, organically-rechargeable, transponder that is powered by a piezoelectric battery, bioelectric battery, thermal battery or any other suitable battery or any combination thereof that utilizes the kinetic energy, the electrical transmission or the heat of the host's body to supply a recharge thereto.

Yet another object of the present invention is to provide a GPS locator system with an implanted, organically-rechargeable transponder having a transmitter that remains dormant until activated by a unique assigned frequency transmitted by a remote unit seeking to locate the subject thereby reducing the amount of charging required to maintain a fully charged battery over an extended period of time regardless of frequency of use.

Still yet another object of the present invention is to provide a locator system with an implanted, organically-rechargeable transponder that is biocompatable with the host organism so as not to be rejected therefrom or to cause an infection thereto.

Another object of the present invention is to provide a locator system with an implanted, organically-rechargeable transponder to aid in preventing and finding kidnapped, abducted or lost individuals.

Another object of the present invention is to provide a locator system with an implanted, organically-rechargeable transponder having an external bioelectric means for providing an additional charge thereto.

Yet another object of the present invention is to provide a locator system with an implanted organically-rechargeable transponder for use as a tool for monitoring public servants during rescue and recovery missions or in dangerous circumstances.

Still another object of the present invention is to provide a locator system having an implanted rechargeable transponder wherein the encoded transponder frequency could provide identification of the implanted subject when authorized to work in secured situations such as airports and military bases.

Yet another object of the present invention is to provide a locator system having a transponder that has a speaker/microphone that is voice activated by a predetermined password and provides for instantaneous two-way communication between the subject and a central office.

Still another object of the present invention is to provide a locator system wherein the transponder could be installed in the black box of an airliner.

Another object of the present invention is to provide a locator system with an implanted, organically-rechargeable transponder that is economical in cost to manufacture and operate.

Yet another object of the present invention is to provide a locator system with an implanted organically-rechargeable transponder that is simple and easy to use.

Additional objects of the present invention will appear as the description proceeds.

The present invention overcomes the shortcomings of the prior art by providing a locator system with an undetectable, inaccessible, implanted piezoelectric transponder that is kinetically regenerated by the natural movements of the implanted subject.

To the accomplishment of the above and related objects, this invention may be embodied in the form illustrated in the accompanying drawings, attention being called to the fact, however, that the drawings are illustrative only, and that changes may be made in the specific construction illustrated and described within the appended claims.

BRIEF DESCRIPTION OF THE DRAWING FIGURES

In order that the invention may be more fully understood, it will now be described, by way of example, with reference to the accompanying drawing in which.

Figure 1:
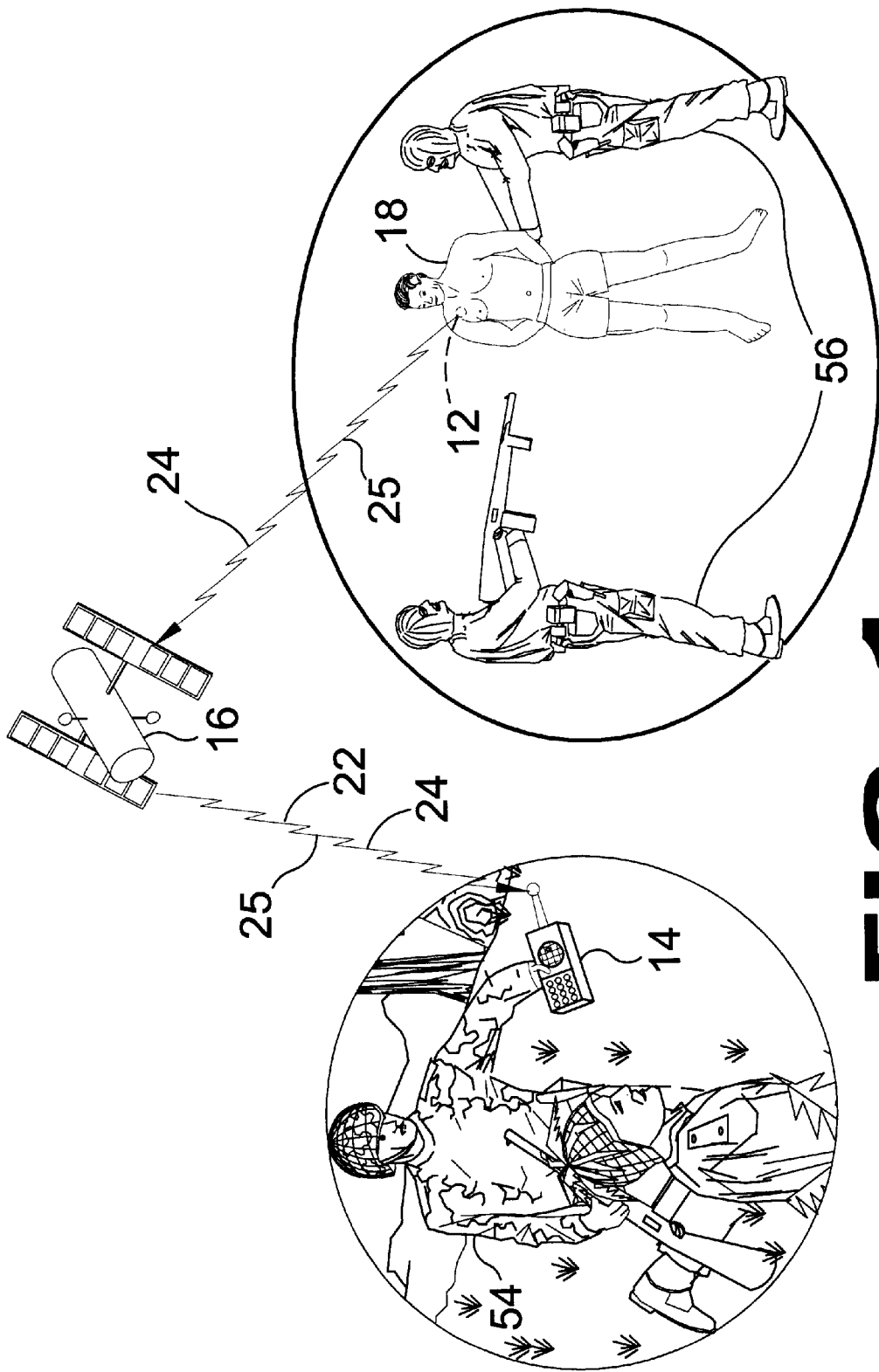
FIG. 1 is an illustrative view of the present invention in use.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

DESCRIPTION OF THE REFERENCED NUMERALS

Turning now descriptively to the drawings, in which similar reference characters denote similar elements throughout the several views, the Figures illustrate the high volume disposable aspirator of the present invention. With regard to the reference numerals used, the following numbering is used throughout the various drawing figures.

10 locator system with implantable transponder
12 transponder
14 locator unit
16 satellite
18 monitored subject
20 transponder transmitter/receiver
22 satellite relay transmission
24 personal encoded frequency
25 positional data
26 rechargeable piezoelectric battery
28 flexible piezoelectric element
30 muscle
32 deltoid
34 pectoralis major
36 bicep
38 transponder receiver
40 locator transmitter
42 locator receiver
44 microprocessor
46 keypad
48 locator display
50 satellite transmitter
52 satellite receiver
62 bioelectric transponder
64 bioelectric battery
66 neuroelectric contact
68 synapse or neuromuscular junction
70 soft tissue
72 thermoelectric contact
74 thermal battery

DETAILED DESCRIPTION OF THE PREFERRED EMBODIMENTS

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

FIG. 1 is an illustrative view of the present invention 10 in use showing an implanted subject 18 captured by enemy soldiers 56 who have taken all his belongings that could have had some kind of transmission or locator device therein but his implanted transponder 12 has been activated by his fellow soldiers 54 who entered the captured soldiers PIN into the keypad 46 of a hand held locator unit 14 which then transmitted a personal encoded frequency 24 unique to his PIN to activate the transponder 12 that is now transmitting the specific location data 25 to the satellite 16.

Figure 2:
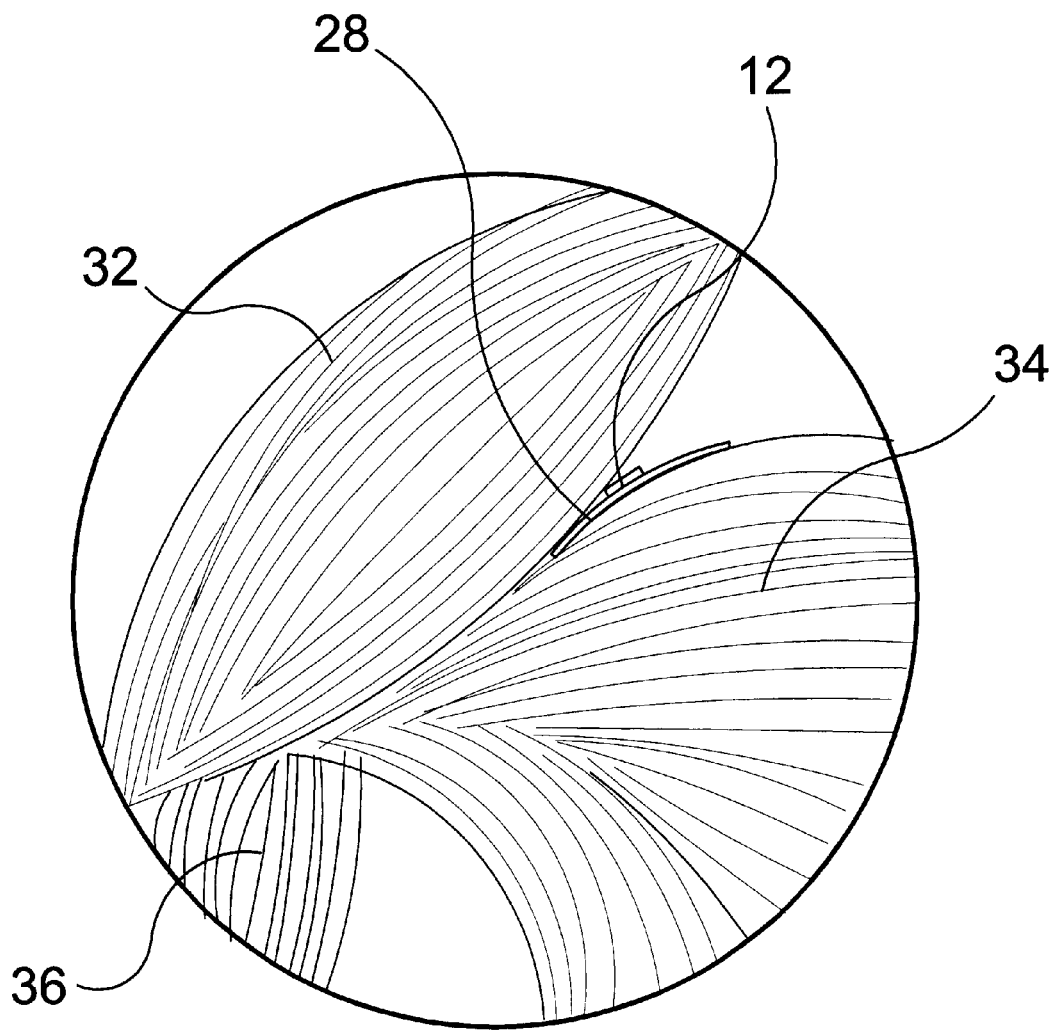
FIG. 2 is an illustrative view of the implanted transponder.

FIG. 2 is an illustrative view of a piezoelectric transponder 58 implanted in muscle tissue 30. A possible implantation point of a piezoelectric transponder 58 is between two large muscles 30 such as the deltoid 32 and the pectoralis major 34 as is shown here. The muscular contraction and extension of those muscles 30 will exert an external force against the piezoelectric element 28 and place a mechanical strain thereupon thus converting the kinetic energy to electrical energy which is then stored in the battery 26.

Figure 3:
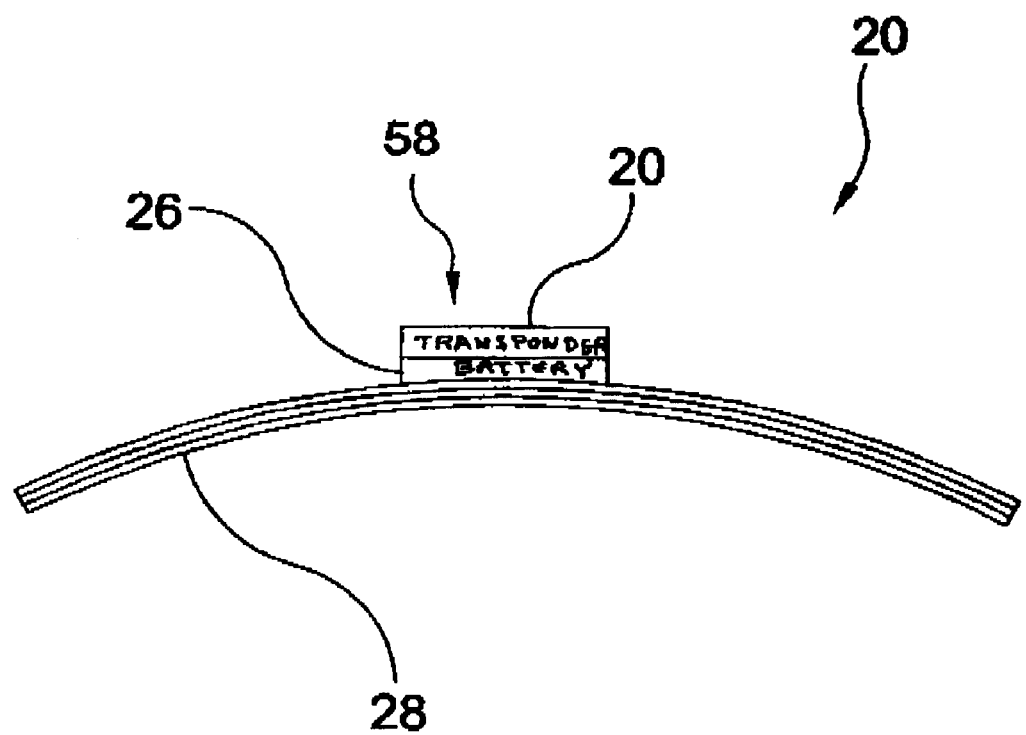
FIG. 3 is a side view of the transponder device.

A side view of the piezoelectric transponder 58 device is shown in FIG. 3 with the transmitter/receiver 20 and battery 26 associated with the flexible piezoelectric element 28.

Figure 4:
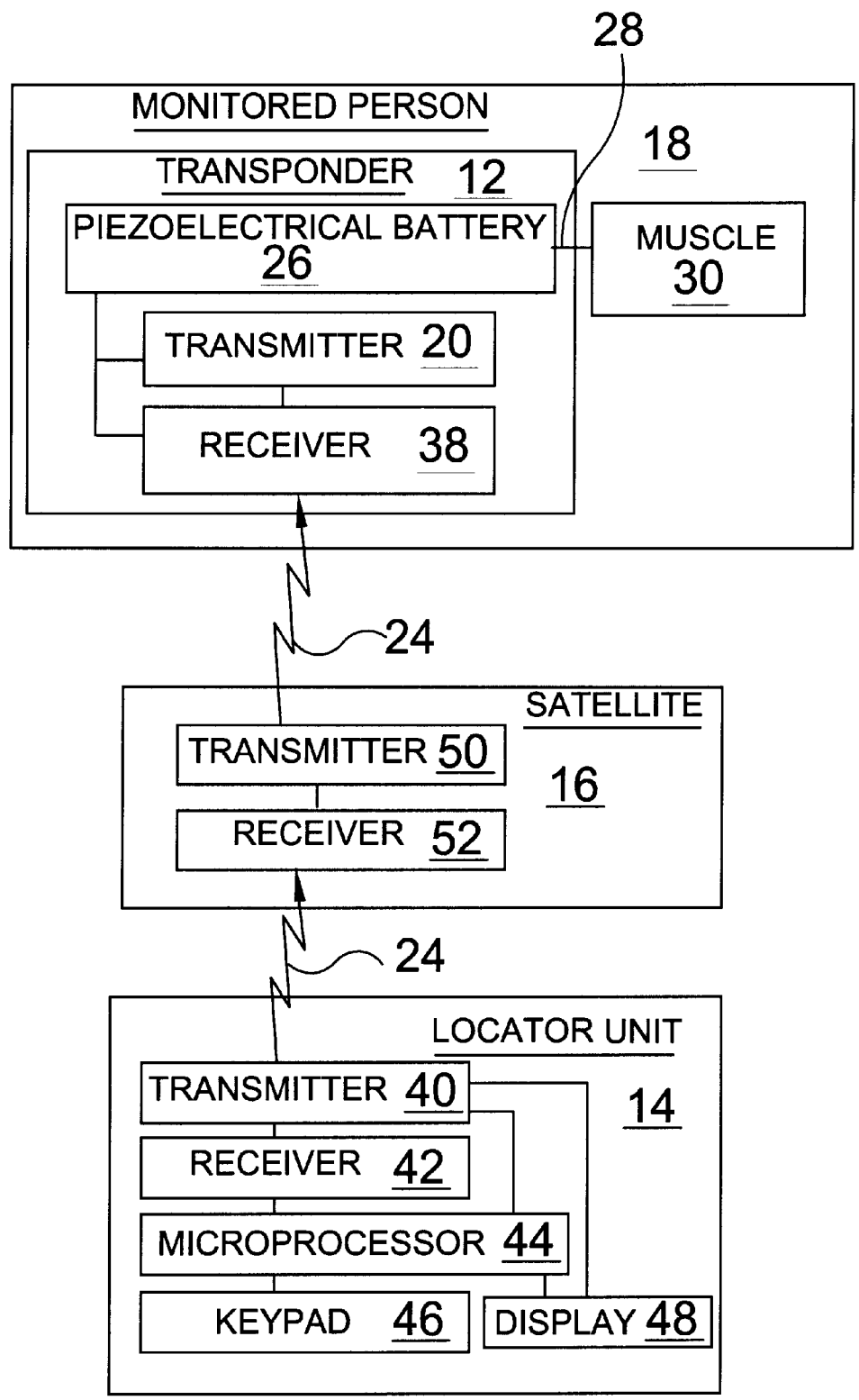
FIG. 4 is a block diagram of the locator unit activating the transponder.
Figure 5:
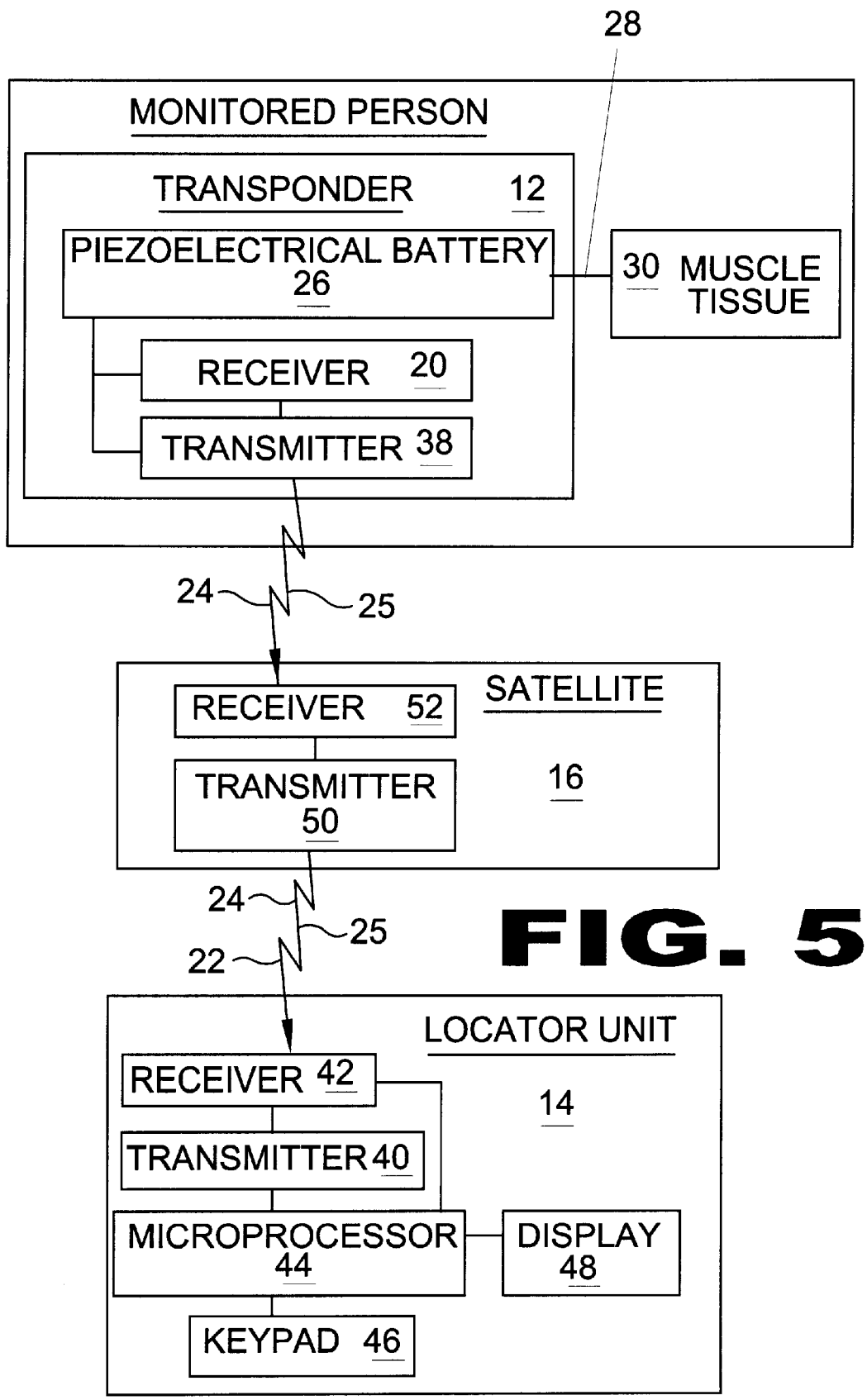
FIG. 5 is a block diagram of the transponder transmitting location data to the locator unit.
Figure 6:
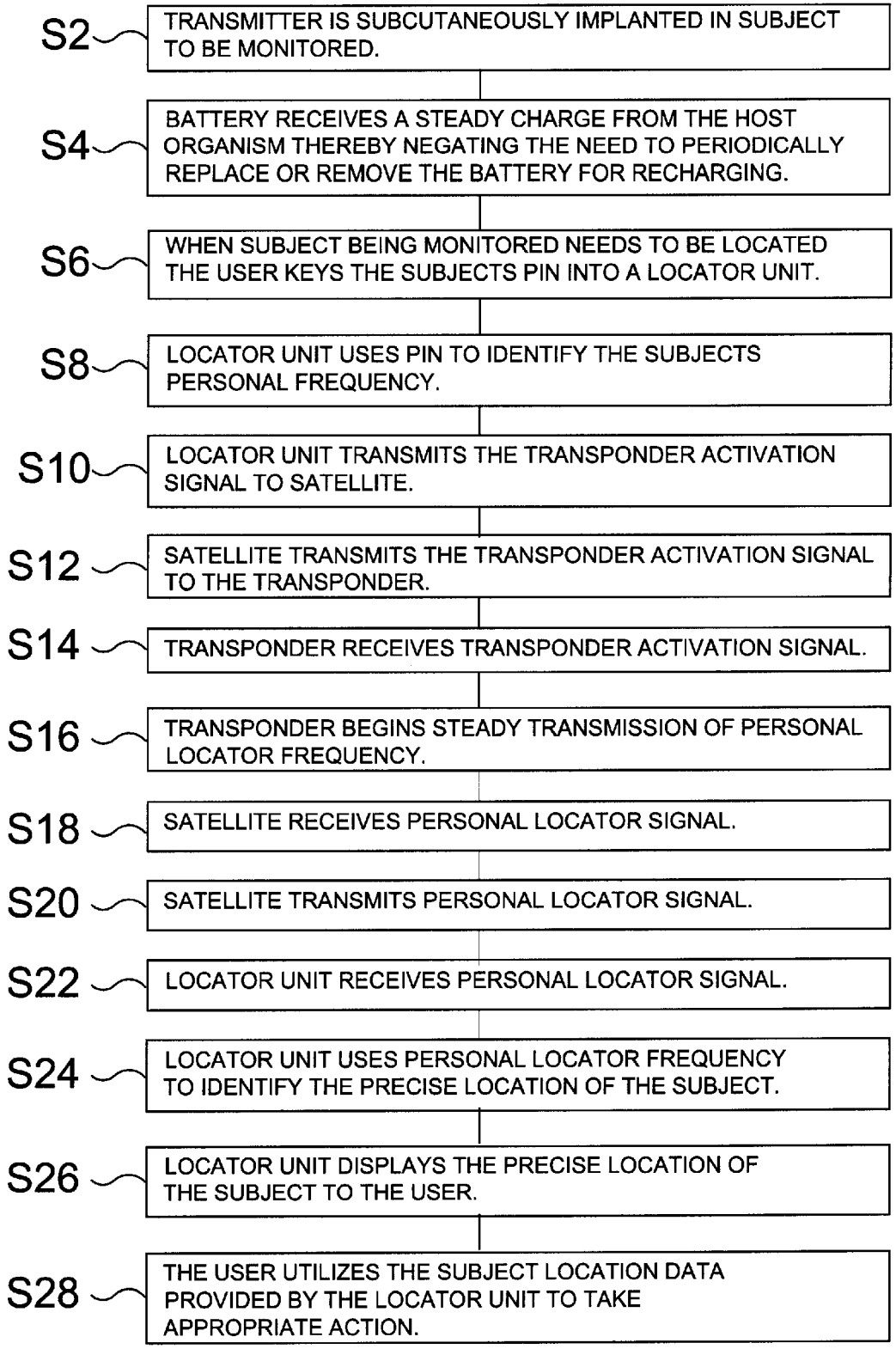
FIG. 6 is a flow chart of the operation of the present invention.

FIG. 4 is a block diagram showing the activation process of a piezoelectric transponder transmitter 58 implanted adjacent a muscle 30 in the monitored subject 18 through the use of a remote locator unit 14 in this case via a satellite 16. The monitored subject's PIN has been entered into the keypad 46 of the locator unit 14 to the microprocessor 44 which translates the PIN and sends the appropriate personal encoded frequency 24 to the implanted piezoelectric transponder 58 thereby activating the transmitter 38 thereof as is demonstrated in FIG. 5. The piezoelectric transponder 58 is transmitting the monitored subjects 18 location data 25 along with the personal encoded frequency 24 back to the locator unit 14 where the microprocessor 44 translates the data to enable the searching party to view the location on the display 48. FIG. 6 is a flow chart showing the aforementioned operation.

Figure 7:
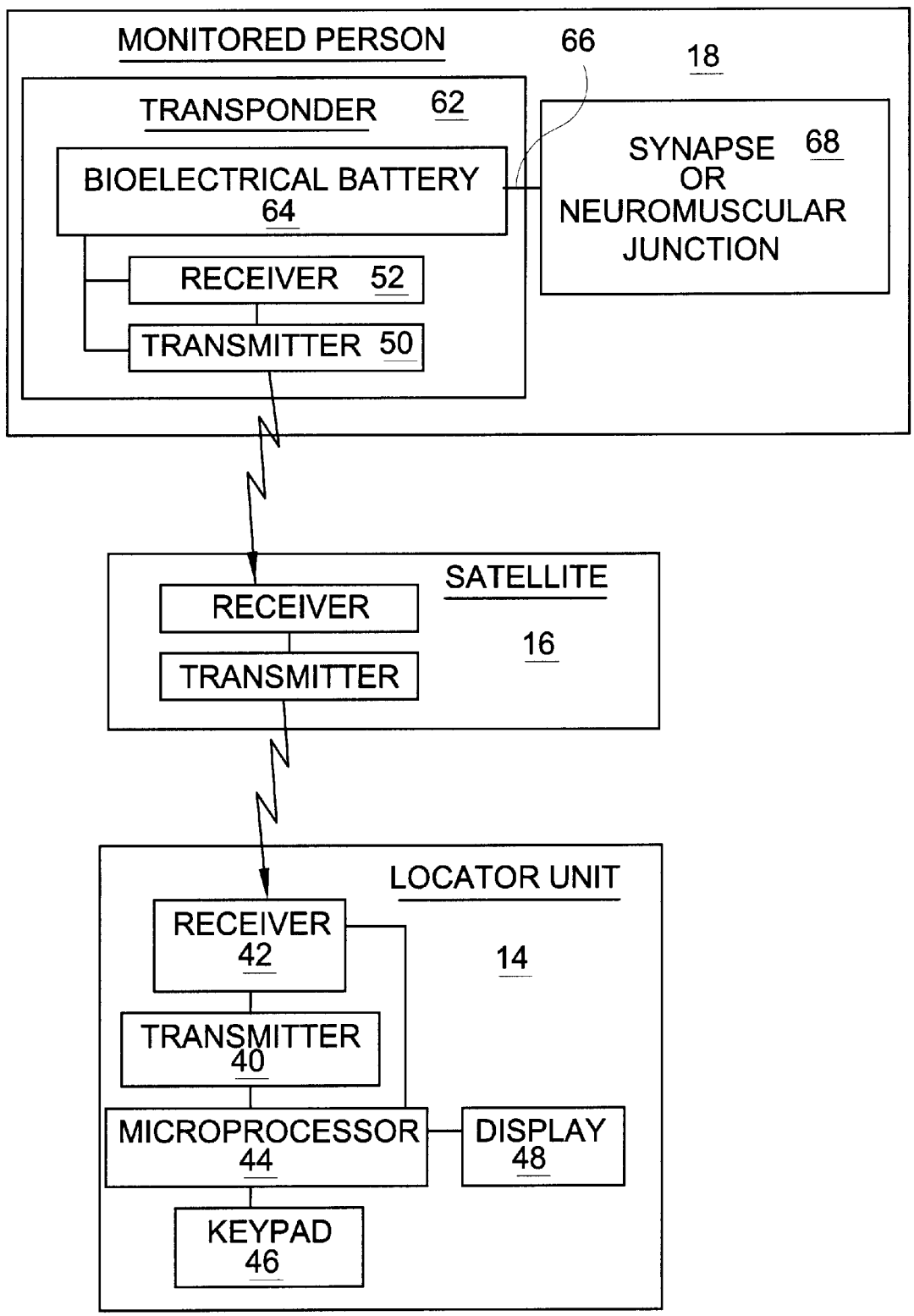
FIG. 7 is a block diagram of the transmission from a bioelectric transponder.

FIG. 7 is a block diagram of a bioelectric transponder transmitter 62 sending precise location data to a remote locator unit 14. The bioelectric battery 64 is recharged by electrical impulses scavenged from neuromuscular junctions or synapses 68.

Figure 8:
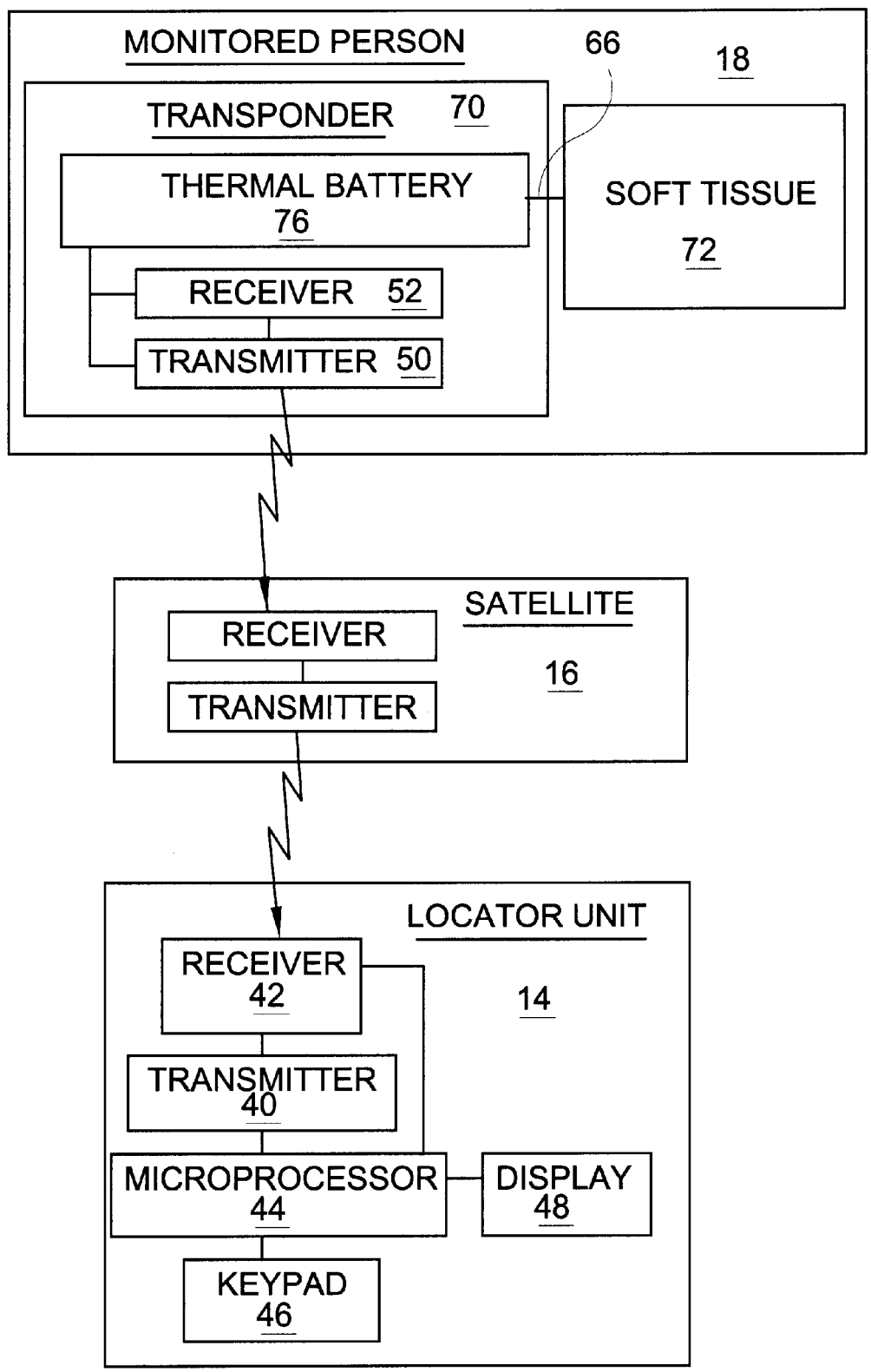
FIG. 8 is a block diagram of the transmission from a thermal transponder.

FIG. 8 is a block diagram demonstrating the transmission process of a thermal transponder 70 transmitter 50 sending data to a remote locator unit 14. The thermal battery 76 is recharged from the heat of the soft tissue 72 in which it is implanted. It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A locator system with an organically-rechargeable transponder that is implanted within the body of a monitored subject, which comprises:
   a) a subcutaneously implantable transponder device comprising:
      i) means for transmitting a specific frequency;
      ii) means for receiving a specific frequency; and
      iii) a bioelectric rechargeable battery having contacts that act as neurotransmitter receptors to scavenge electricity from areas with high concentration of action potential where synaptic or neuromuscular transmission occur;
   b) a remote locator unit including:
      i) means for entering a personal identification number, hereinafter referred to as PIN, unique to said subject;
      ii) microprocessor for translating said PIN to a preselected personal encoded frequency unique to said subject and for interpreting location data received by said transponder;
      iii) means for transmitting said personal encoded frequency to said transponder;
      iv) means for receiving said location data from said transponder; and
      v) means for displaying said location data.

2. A locator system with an organically-rechargeable transponder implanted within the body of the monitored subject as recited in claim 1, in which said bioelectric battery has an external secondary means of recharging by passing an electrical current through the body of said monitored subject.

3. A locator system with an organically-rechargeable transponder implanted within the body of the monitored subject as recited in claim 2, in which said secondary recharging means comprises:
   a) a power source;
   b) means for transferring electricity from said power source to said monitored subject; and
   c) means for regulating the voltage and current transferred from said power source to said monitored subject.

4. A locator system with an organically-rechargeable transponder implanted within the body of the monitored subject as recited in claim 2, in which said secondary recharging means uses high frequency current that passes through all body tissue thereby enabling the battery to accept a more efficient charge.

5. A locator system with an organically-rechargeable transponder implanted within the body of the monitored subject as recited in claim 1, in which said transponder further includes a means for receiving and interpreting voice commands to enable the user to enable the transponder by speaking a predetermined password.

6. A locator system with an organically-rechargeable transponder implanted within the body of the monitored subject as recited in claim 5, in which said transponder further includes a speaker and microphone means to provide for two-way communication between the monitored subject and the remote locator unit.

7. A locator system with an organically-rechargeable transponder that is implanted within the body of a monitored subject, which comprises:

a) a subcutaneously implantable transponder device comprising:
  i) means for transmitting a specific frequency;
  ii) means for receiving a specific frequency;
  iii) a rechargeable battery; and
  iv) means for recharging said battery comprising a piezoelectric transponder having a flexible piezoelectric element, said piezoelectric element having a first face and a second face composed of a crystalline substance that develops an electrostatic potential when mechanically strained by an external source, said electrostatic potential providing an electric charge to said battery, and said transponder being implanted between two large muscles in such a manner that the contraction and extension of said muscles will exert an external force against said piezoelectric element placing a mechanical strain on said piezoelectric element thereby generating the electrostatic potential;
b) a remote locator unit including:
  i) means for entering a personal identification number, hereinafter referred to as PIN, unique to said subject;
  ii) microprocessor for translating said PIN to a preselected personal encoded frequency unique to said subject and for interpreting location data received by said transponder;
  iii) means for transmitting said personal encoded frequency to said transponder;
  iv) means for receiving said location data from said transponder; and
  v) means for displaying said location data.

8. The method of locating a subject comprising the steps of:
a) implanting subcutaneously a transponder device in said subject, said transponder device:
  i) transmitting a specific frequency;
  ii) receiving a specific frequency; and
  iii) activating said transponder device using a bioelectric rechargeable battery having contacts that act as neurotransmitter receptors to scavenge electricity from areas with high concentration of action potential where synaptic or neuromuscular transmission occur; and
b) using a remote locator unit to locate said subject:
  i) entering a personal identification number (PIN) into said remote locater unit, said PIN unique to said subject;
  ii) using a microprocessor to translate said PIN to a preselected personal encoded frequency unique to said subject and for interpreting location data received by said transponder;
  iii) transmitting said personal encoded frequency to said transponder;
  iv) receiving said location data from said transponder; and
  v) displaying said location data.

9. The method of locating a subject comprising the steps of:
a) implanting subcutaneously a transponder device in the body of the subject, said transponder device:
  i) transmitting a specific frequency;
  ii) receiving a specific frequency;
  iii) using a rechargeable battery to energize said transponder device; and
  iv) recharging said battery by using a piezoelectric transponder having a flexible piezoelectric element, said piezoelectric element having a first face and a second face composed of a crystalline substance that develops an electrostatic potential when mechanically strained by an external source, said electrostatic potential providing an electric charge to said battery, and said transponder being implanted between two large muscles in such a manner that the contraction and extension of said muscles will exert an external force against said piezoelectric element placing a mechanical strain on said piezoelectric element thereby generating the electrostatic potential;
b) using a remote locator unit to locate said subject by:
  i) entering a personal identification number (PIN) unique to said subject;
  ii) translating said PIN to a preselected personal encoded frequency unique to said subject and interpreting location data received by said transponder;
  iii) transmitting said personal encoded frequency to said transponder;
  iv) receiving said location data from said transponder; and
  v) displaying said location data.

\* \* \* \* \*